US005683907A

United States Patent [19]
Johnson

[11] Patent Number: 5,683,907
[45] Date of Patent: Nov. 4, 1997

[54] METAL ION-LIGAND COORDINATION COMPLEXES, ANTIBODIES DIRECTED THERETO, AND ASSAYS USING SUCH ANTIBODIES

[75] Inventor: David K. Johnson, Vernon Hills, Ill.

[73] Assignee: Abbott Laboratories, Abbott Park, Ill.

[21] Appl. No.: 435,603

[22] Filed: May 5, 1995

Related U.S. Application Data

[62] Division of Ser. No. 176,360, Dec. 30, 1993, Pat. No. 5,476,939.

[51] Int. Cl.$^6$ .................. G01N 33/543; G01N 33/20; A23J 1/00
[52] U.S. Cl. .................. 436/518; 436/74; 436/77; 436/84; 436/172; 436/800; 436/804; 435/7.9; 435/7.93; 435/968; 530/413
[58] Field of Search .................. 435/7.9, 7.93, 435/968; 436/74, 77, 84, 172, 800, 804, 518; 530/413

[56] References Cited

U.S. PATENT DOCUMENTS

| | | |
|---|---|---|
| 4,474,893 | 10/1984 | Reading . |
| 4,476,229 | 10/1984 | Fino . |
| 4,510,251 | 4/1985 | Kirkemo . |
| 4,614,823 | 9/1986 | Kirkemo . |
| 4,668,640 | 5/1987 | Wang . |
| 4,676,980 | 6/1987 | Segal . |
| 4,722,892 | 2/1988 | Meares . |
| 4,816,567 | 3/1989 | Cabilly . |
| 5,053,226 | 10/1991 | Rosenblum et al. . |
| 5,189,178 | 2/1993 | Galardy . |
| 5,239,078 | 8/1993 | Galardy . |

OTHER PUBLICATIONS

*Chromatography: a Laboratory Handbook of Chromatographic and Electrophoretic Methods*, Third Edition, Edited by Erich Heftmann, published by Van Nostrand Reinhold Co., 1975, (Chapter 16, "Chromatography of Proteins", Hugo Fasold) pp. 512–515.
Science Reports, A. Cochran, et al., Antibody–Catalyzed Porphyrin Metallation, vol. 249, (Aug. 17, 1990) pp. 781–783.
Journal of Immunological Methods, R.W. Gillette, Development and characterization of monoclonal antibodies with specificity for metallic radioisotope chelators linked to antibodies and other proteins, vol. 124, (1989) pp. 277–282.
The Journal of Nuclear Medicine, D.A. Goodwin, et al., Pre–Targeted Immunoscintigraphy of Murine Tumors with Indium–111–Labeled Bifunctional Haptens, 29 (1988) pp. 226–234.
Pure & Appl. Chem., E. Keinan, et al., Towards antibody–mediated metalloporphyrin chemistry, vol. 62, No. 10 (1990) pp. 2013–2019.
Nature, G. Kohler, et al., Continuous cultures of fused cells secreting antibody of predefined specificity, vol. 256 (Aug. 7, 1975) pp. 495–497.
Cancer Research, C. Kosmas, et al., Development of Humoral Immune Responses against a Macrocyclic Chelating Agent (DOTA) in Cancer Patients Receiving Radioimmunoconjugates for Imaging and Therapy, vol. 52 (Feb. 15, 1992) pp. 904–911.
Cancer Research, J. Le Doussal, et al., Targeting of Indium 111–labeled Bivalent Hapten to Human Melanoma Mediated by Bispecfic Monoclonal Antibody Conjugates: Imaging of Tumors Hosted in Nude Mice, vol. 50 (Jun. 1, 1990) pp. 3445–3452.
Biochemistry, R. Love, et al., How the Anti–(Metal Chelate) Antibody CHA255 is Specific for the Metal Ion of Its Antigen: X–ray Structures for Two Fab'/Hapten Complexes with Different Metals in the chelate, vol. 32, No. 41 (1993) pp. 10950–10959.
Bioconjugate Chem., V. Philomin, et al., Synthesis of Cobalt Carbonyl Complexes of Cortisol and Testosterone. Study of Their Recognition by Specific Polyclonal Antibodies, vol. 4 (1993) pp. 419–424.
Nature, D.T. Reardan, et al., Antibodies against metal chelates, vol. 316 (Jul. 18, 1985) pp. 265–268.
Journal American Chemical Society, A.W. Schwabacher, et al., Metalloselective Anti–Porphyrin Monoclonal Antibodies, vol. 111 (1989) pp. 2344–2346.
Cancer Research, M.J. Tilby, et al., Sensitive Detection of DNA Modifications induced by Cisplatin and Carboplatin in Vitro and in Vivo Using a Monoclonal Antibody, vol. 51, (Jan. 1991) pp. 123–129.
The Journal of Nuclear Medicine, M. Zoller, et al., Establishment and Characterization of Monoclonal Antibodies Against an Octahedral Gallium Chelate Suitable uitable for Immunoscintigraphy with PET, vol. 33, No. 7 (Jul. 1992) pp. 1366–1372.
Dialog Alert DA389, Polypeptide used in imaging and treatent of carcinomas and tumors–comprising substd antibody CDR having binding affinity for metal chelate of EDTA or DETA or analogues, 1994 Derwent Info Ltd., *abstract*.

*Primary Examiner*—Paula K. Hutzell
*Assistant Examiner*—Benet Prickril
*Attorney, Agent, or Firm*—David L. Weinstein

[57] ABSTRACT

The present invention relates to the field of immunossays for metal ions. The invention presents: metal ion-ligand coordination complexes ("MLC"), novel ligands, antibodies specific for MLC, immunoassays utilizing the foregoing, and methods for selecting said antibodies.

2 Claims, 12 Drawing Sheets

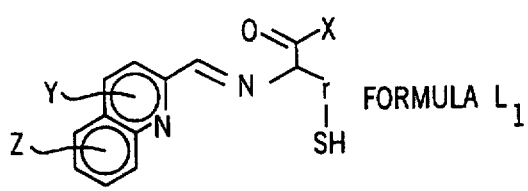 FORMULA $L_1$

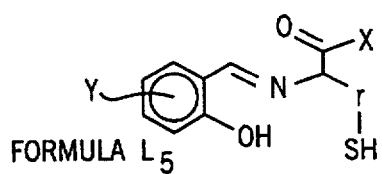 FORMULA $L_5$

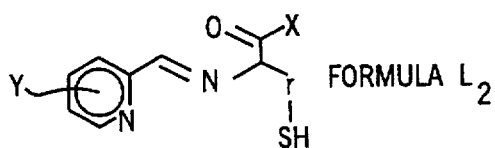 FORMULA $L_2$

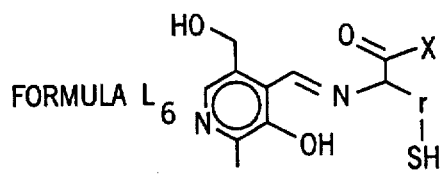 FORMULA $L_6$

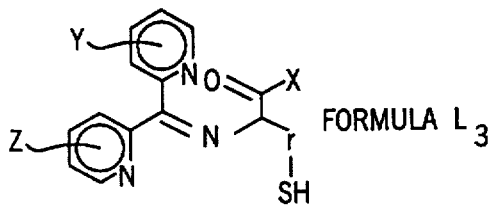 FORMULA $L_3$

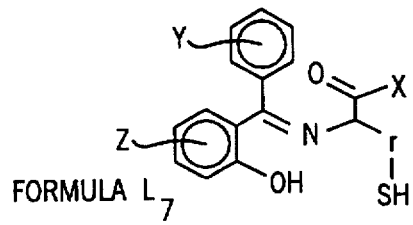 FORMULA $L_7$

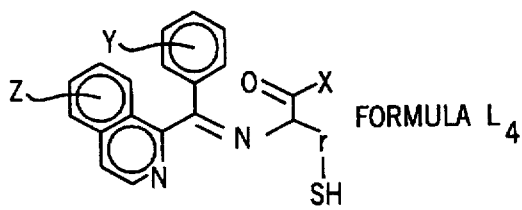 FORMULA $L_4$

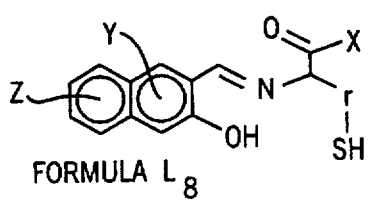 FORMULA $L_8$

WHERE r IS SELECTED FROM THE GROUP CONSISTING OF $\{ -CH_2-,\ -(CH_2)_2-,\ -(C(CH_3)_2)- \}$ $R_1$ IS $C_1$–$C_4$ ALKYL OR —N(succinimide)

$R_2$ IS $C_1$–$C_4$ ALKYL $R_3$ IS $C_1$–$C_{10}$ ALKYL CONTRIBUTED BY A CONJUGATE MOLECULE

Y AND Z CAN BE THE SAME OR DIFFERENT AND ARE SELECTED FROM THE GROUP CONSISTING OF $\{ -H,\ -CO_2H,\ -SO_3H \}$

X IS SELECTED FROM THE GROUP CONSISTING OF $\{ -OH,\ -OR_1,\ -NHR_2,\ -NHR_3 \}$

FIG. 1 where M is a metal atom r is defined as in Figure 1 where M is a metal atom
r is defined as in Figure 1

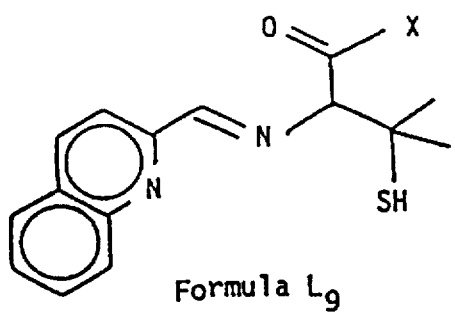
Formula $L_9$
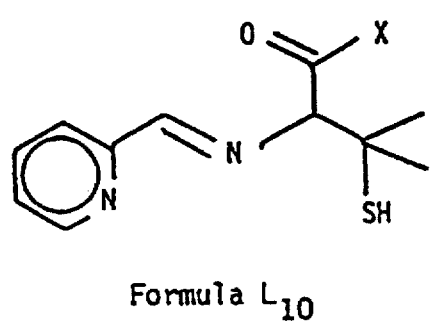
Formula $L_{10}$
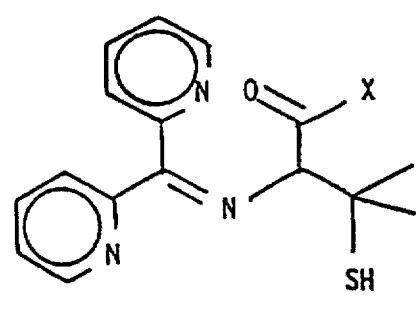
Formula $L_{11}$
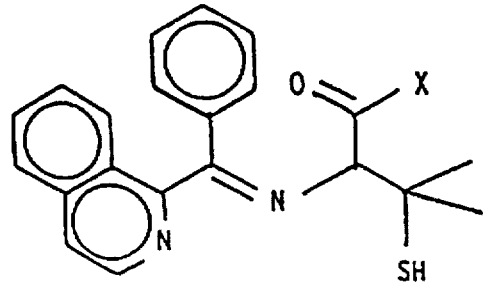
Formula $L_{12}$
X is as defined in Figure 1
FIG. 4

Formula M₁

X is defined as in Figure 1

Formula L₁₆ n is 0 or 1

M is Pb, Zn, Cu, Hg, Cd, Ni, Fe, Co, Bi

Formula $M_5$

Formula M₆

$M = Pb^{2+}$

METAL ION-LIGAND COORDINATION COMPLEXES, ANTIBODIES DIRECTED THERETO, AND ASSAYS USING SUCH ANTIBODIES

This application is a division of U.S. patent application Ser. No. 08/176,360, filed Dec. 30, 1993 now U.S. Pat. No. 5,476,959.

FIELD OF THE INVENTION

The present invention relates to the field of immunoassays for metal ions.

BACKGROUND OF THE INVENTION

Monoclonal antibodies specific for a complex comprising a chelating agent and a metal ion are disclosed in U.S. Pat. No. 4,722,892 to Meares et al. Also disclosed therein is the detection or separation of metal ions from a solution containing other metals, e.g. by adding the chelating agent to the solution and passing the solution over a solid phase to which the antibodies have been pre-bound. The antibodies thus capturing the complex of chelating agent and metal ion.

U.S. Pat. Nos. 5,239,078 and 5,189,178 to Galardy et al. disclose raising antisera by immunizing an animal with a chelator (coupled to an immunogenic carrier) which is capable of binding a metal ion at a one to one ratio. The antibodies are useful for in vitro assay of biological fluid samples to monitor the therapeutic or prophylaxic regimens of patients receiving the chelator.

Tilby et al. disclose antibodies which specifically bind to a complex of DNA and platinum dichloride instead of dichloro-diamino-platinum (Tilby et al., Cancer Res., 51, 123–129 (1991)). Dichioro-diamino-platinum is administered to ovarian cancer patients and it reacts with the DNA in growing cells, such as cancer cells, to form the complex of guanidine and platinum dichloride and thereby disrupting the DNA and causing cell death. The antibodies are useful for in vitro assay of patients' samples for the formation of the complex of guanidine and platinum dichloride, to determine the response of the patients to the treatment.

Philomin et al. disclose the synthesis of cobalt carbonyl complexes of cortisol and testosterone and polyclonal antibodies specific for the steroid ligand but not the cobalt metal ion in the complexes (Philomin, et al., *Bioconjugate Chem.*, 4, 419–424 (1993)). Philomin et al. also suggest the use of these organometallic complexes as tracers in nonisotopic carbonyl-metal immunoassays. supra.

U.S. Pat. No. 5,053,226, to Rosenblum et al. discloses monoclonal antibodies specifically binding one of the two ligands (i.e. 1,2-diaminocyclohexane but not sulfate) of a ternary platinum (II) complex: disodium 1,2-diaminocyclohexane platinum sulfate complex.

Fluorescent polarization techniques are based on the principle that a fluorescent labelled compound when excited by linearly polarized light will emit fluorescence having a degree of polarization inversely related to its rate of rotation. Therefore, when a fluorescent labelled tracer-antibody complex is excited with linearly polarized light, the emitted light remains highly polarized because the fluorophore is constrained from rotating between the time light is absorbed and emitted. When a "free" tracer compound (i.e., unbound to an antibody) is excited by linearly polarized light, its rotation is much faster than the corresponding tracer-antibody conjugate and the molecules are more randomly oriented, therefore, the emitted light is depolarized. Thus, fluorescent polarization provides a quantitative means for measuring the amount of tracer-antibody conjugate produced in a competitive binding immunoassay.

U.S. Pat. Nos. 4,510,251 and 4,614,823, to Kirkemo et al., disclose fluorescent polarization immunoassays (FPIA) for ligands using aminomethylfluorescein derivatives as tracers, and the aminomethylfluorescein derivatives, respectively. U.S. Pat. No. 4,476,229, to Fino et al., discloses substituted carboxyfluoresceins, including those containing a thyroxine analog, for use in fluorescence polarization immunoassays. U.S. Pat. No. 4,668,640, to Wang et al., discloses fluorescence polarization immunoassay utilizing substituted carboxyfluoresceins.

Examples of commercially available FPIA are those for thyroxine such as IMx®, TDx®, and TDxFLx™ T$_4$ assays (Abbott Laboratories, Abbott Park, Ill.).

SUMMARY OF THE INVENTION

One aspect of the invention presents a metal ion-ligand coordination complex (the complex is herein referred to as an "MLC") comprising two or more ligands bound to a metal ion. The preferred MLC is a ternary MLC (herein referred to as a "TMLC").

Another aspect of the invention presents novel ligands capable of binding metal ions. The novel ligands can be used in any of the above aspects of the invention.

Another aspect of the invention presents an MLC with a protein carrier attached thereto to form an MLC-protein conjugate which is preferably immunogenic.

Another aspect of the invention presents a method using MLC-protein conjugate for the production of antibodies specific to the MLC. Also presented is a method for screening antibodies that bind the MLC, and a method for screening for antibodies that are not cross-reactive with MLC containing metal ion that is not of interest. Thus, also presented is a solid phase, to which the MLC is attached, useful for such screening.

Another aspect of the invention presents the antibodies produced according to the above method. Preferably, these antibodies react with an epitope that combines structural features of at least two ligands in an MLC while showing minimal reactivity with either the ligand individually or with the metal ion itself.

Another aspect of the invention presents a method which uses two or more ligands for binding to a metal ion of interest to form an MLC. Preferably, this method is applied to an in vitro or in vivo assay for a metal ion by detecting the resulting MLC. Preferably, the detection is by means of the specific binding of a binding agent to the MLC to form a complex (the complex is herein referred to as "MLC-binding agent"). More preferably, the binding agents are the above antibodies. The method may also be applied to an in vitro or in vivo removal of the metal ion by removing the resulting MLC-binding agent.

Another aspect of the invention presents the MLC-binding agent.

BRIEF DESCRIPTION OF THE DRAWINGS

FIG. 1 presents the structures of preferred ligands.

FIG. 4 presents the preferred novel ligands, in particular, for binding to lead ions.

DETAILED DESCRIPTION OF THE INVENTION

Figure 2:
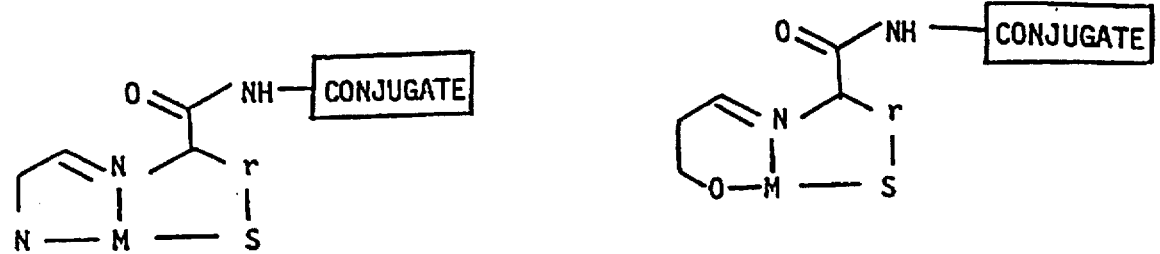
FIG. 2 schematically shows an MLC-protein conjugate in which the protein is linked to the MLC via the carboxyl group on the MLC.

The present invention presents binding agents which specifically bind to metal ion-ligand coordination complexes based on their shapes. The metal ion-ligand coordination complexes are hereinafter referred to as "MLC". Preferably, the binding agents are biological binding agents. The preferred biological binding agents are antibodies specific for MLC having two or more ligand molecules. These antibodies are preferably raised against an immunogen in which the MLC is attached to a carrier protein via one of the ligands. The invention discovers that antibody recognition of a metal ion of interest is more specific if the MLC has two or more ligand molecules, as opposed to the prior art antibodies which were raised against protein conjugates of binary MLC.

The greater number of degrees of freedom intrinsic in a 3-component (or higher) multimolecular complex compared to its 2-component counterpart results in a wider range of possible ligand conformations and ligand-metal stoichiometries and hence a greater likelihood that a particular shape exists that is unique to the particular metal ion of interest. Prior art antibodies recognize rigid binary complexes, such as EDTA chelates and porphyrins, the shapes of which vary little from one metal to the next as they are largely determined by steric constraints inherent in the ligands themselves ("ligand-driven" shape). Such antibodies thus exhibit low specificity for a metal ion of interest and have not proven useful in, for example, detecting a given metal ion in a sample containing other, non-target metal ions.

The present invention increases specificity because the shapes of TMLC (and those with larger numbers of ligands) are determined by the nature of the metal ion (i.e. display "metal ion-driven" shape) to a far greater extent than are those of binary complexes. When shape is metal ion-driven, shape-selective antibodies can be obtained that, for a fixed set of ligands, display high specificity for a given metal ion when presented in the form of the MLC.

These ligands and/or antibodies can be used for example, to assay for or remove toxic metals in a sample, e.g. lead levels in biological samples or mercury levels in industrial waste or water treatment plants. They can also be used to assay for the therapeutic levels of metals in biological samples, such as the level of gold in a patient who is administered gold to treat his rheumatoid arthritis. They can further be used to assay levels of endogenous metal ions, such as iron, copper, chromium, cobalt, etc.

The present invention also presents novel ligands useful for the above purposes. These ligands can additionally be used to remove metals from a sample, such as to remove toxic metals from industrial samples, to scavenge silver from photographic processing solutions. The ligands can additionally be administered in vivo (therapeutically) to treat patients suffering from metal poisoning, such as lead poisoning.

The metals described herein can be any metal of interest.

The present invention also describes criteria for selecting the appropriate ligands for the above objectives.

The present invention also presents antibodies specific to a MLC, wherein the specificity is metal-ion driven.

The following elaborates the foregoing outlines of the invention.

Metal Ion-Ligand Coordination Complex (MLC)

An MLC consists of a central metal ion bound to a number of other molecules, termed ligands. The nature of the chemical bond formed between a ligand and a metal can be thought of as involving the donation of a pair of electrons present on the ligand molecule or, in molecular orbital terms, as a molecular orbital formed by combining a filled orbital of the ligand with a vacant orbital of the metal. Those atoms in the ligand molecule that are directly involved in forming a chemical bond to the metal ion are therefore termed the donor atoms and these generally comprise elements of Groups V and VI of the periodic table, with nitrogen, oxygen, sulfur, phosphorus and arsenic being those most commonly employed.

Molecules that contain two or more donor atoms capable of binding to a single metal ion are termed chelating agents, or chelators, and the corresponding metal complexes are called chelates. The number of donor atoms present in a given chelator is termed the denticity of that chelator, ligands possessing two donor sites being called bidentate, those with three donor sites, tridentate, and so forth. In general, the higher the denticity of a chelator the more stable are the chelates formed, up to the point at which the denticity of the chelator matches the maximum coordination number attainable by the particular metal ion of interest. The maximum coordination number of a given metal ion in a given oxidation state is an intrinsic property of that metal, reflecting the number of vacant orbitals and, hence, the number of chemical bonds it is able to form with ligand donor atoms. When all of the available vacant orbitals have been used to form bonds to donor atoms in the ligand or ligands, the metal is said to be coordinatively saturated.

Ligands

In the present invention, the number of ligands involved in the MLC must be at least two and, depending on the metal ion of interest, may be as many as eight. The number of ligands in any given complex will be determined by the nature of the particular metal ion (primarily its maximum coordination number) and the nature of the ligands selected (their denticity, donor atom set, charge, size, etc.). It is not required that the antibody combining site recognize features on all of the ligands present in the complex. As long as the antibody recognizes a combination of at least two ligands, additional ligands which do not contribute to the epitope may be present to stabilize the complex or to enhance other properties such as aqueous solubility.

For any given metal ion, useful ligands according to the present invention may be selected by one skilled in the art, employing the following criteria. Ligands must possess donor atoms (or sets of donor atoms in the case of chelating ligands) that favor binding to the target metal ion, the general preference of any given metal ion for particular donor atoms (generally selected from the group consisting of caboxylic, phenolic or ether oxygen atoms; amine, imine or aromatic nitrogen atoms and charged or neutral sulfur atoms) being well known in the art.

It is not essential that any of the ligands that do contribute to the epitope recognized by an antibody according to the present invention be chelating ligands. Though ligands suitable for use in the present invention are preferably chelating ligands, the presence of a chelating ligand is not essential as non-chelating ligands such as certain phosphines and sugar analogs, can also be useful. The only requirement is that the antibody recognizes a combination of at least two ligands in the coordination sphere of an MLC and these ligands can be either monodentate or of higher denticity.

However, the ligands must also offer the prospect of forming ligand-metal linkages that are likely to remain stable in vivo i.e. the ligand-metal linkage does not dissociate during the time required to raise an immune response to the complex (generally several months). For many metals of interest there exists considerable art relating to the in vivo stability of particular ligand-metal linkages, which may be used to guide ligand selection. For many metal ions of interest, this requirement favors the selection of chelating ligands, as chelating ligands generally form coordination complexes of higher thermodynamic stability than do corresponding combinations of monodenate ligands.

Useful chelating ligands that form highly stable MLC with many metal ions include polyaminopolycarboxylic acids such as ethylenediaminetetraacetic acid (EDTA) and diethylenetriaminepentaacetic acid (DTPA) and phenol-containing aminopolycarboxylates such as N,N'-bis (hydroxybenzyl)ethylenediamine-N,N'-diacetic acid (HBED). These chelators have a denticity of 6 or higher and, as most transition and main group metals have a maximum coordination number of 6, the resulting species are coordinatively saturated binary MLC i.e. complexes consisting of a single ligand molecule and a single metal ion.

Preferred antibodies according to the present invention recognize MLC comprising the metal ion of interest plus 2 or 3 ligands, with those containing 2 ligands being particularly preferred.

In cases where there is no direct art concerning in vivo stability, art relating to the thermodynamic and/or kinetic stability of various ligand-metal combinations may be used as a basis for ligand selection.

A further requirement is that each of those ligands that comprise the epitope recognized by an antibody according to the present invention be bifunctional. A bifunctional ligand is a molecule that contains, in addition to at least one metal binding site (donor atom), a second reactive moiety through which the ligand may be covalently linked to, for example, a protein, a solid phase or a label, without significantly affecting the metal-binding properties of the ligand. Bifunctionality of the ligands is essential for configuring screening assays used to identify and select monoclonal antibodies that are specific for MLC, for preparing affinity chromatography media used to purify such antibodies and for preparing antigen-label tracers for use in immunoassays.

One skilled in the art will readily recognize positions within a given ligand molecule where incorporation of an additional reactive moiety will not affect metal-binding properties and will also readily recognize reactive moieties that are useful in coupling the ligand to another molecule or solid phase. Ligands should also be selected such that they contain a highly differentiated organic framework, incorporating wherever possible aromatic structures, rigid ring systems and asymmetric carbon centers. Having selected the donor atom set, denticity, bifunctional side arm and organic framework of the ligands, the stoichiometry of the resulting target MLC (i.e. whether ternary or of higher molecularity) will be dictated by the maximum coordination number of the particular metal ion of interest.

In addition to displaying bifunctionality and stable ligand-metal binding in vivo, preferred ligands also incorporate structural features that are thought to contribute to immunogenicity and differential recognition by proteins. Such structural features include aromatic ring systems (Zoller, et al, *J. Nucl. Med.*, 33, 1366–72 (1992)), rigid cyclic structures (Kosmas, et al, *Cancer Res.*, 52, 904–11 (1992)) and asymmetric carbon centers (Reardon, et al, *Nature*, 316, 265–68 (1985); Zoller, et al, *J. Nucl. Med.*, 33, 1366–72 (1992)).

Preferred Ligands

Preferred ligands are tridentate chelators that are bifunctional and have aromatic character. A particularly preferred group of such ligands is formed by the Schiff base condensation of a sulfhydryl-containing amino acid with aromatic aldehydes or ketones that contain a donor atom (nitrogen or oxygen) positioned 2 or 3 carbon atoms distant from the aldehyde (or ketone) oxygen atom. The aromatic ring systems are optionally derivatized with negatively charged groups, to increase immunogenicity and aqueous solubility. Of these, the ligands shown in FIG. 1 are particularly preferred. These ligands are also herein referred to as $L_1$ to $L_8$. As far as the inventor is aware, these ligands are novel except for $L_6$ when its r is $CH_2$ and its X=OH.

Figure 3:
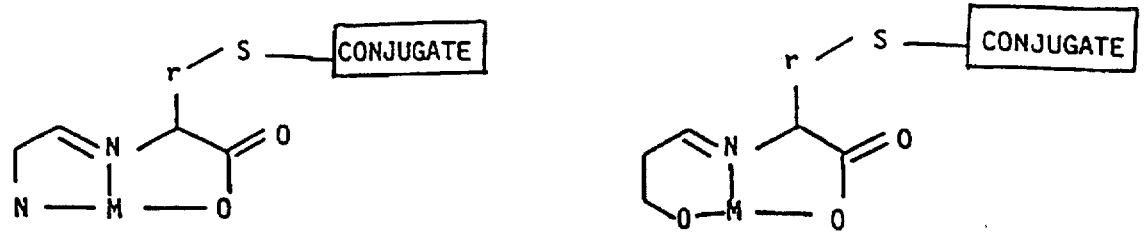
FIG. 3 schematically shows an MLC-protein conjugate in which the protein is linked to the MLC via the sulfhydryl group on the MLC.

The parent ligands ($L_1$ to $L_8$, where X is —OH) are potentially tetradentate, providing in all cases one sulfhydryl donor, one imine nitrogen donor, one carboxylate oxygen donor and either an aromatic nitrogen donor ($L_1$–$L_4$) or a phenolic oxygen donor ($L_5$–$L_8$). When used in the present invention, the ligands are linked to other molecules through either the carboxylate function or the sulfhydryl function, leaving three remaining donor sites. The carboxylate-linked ligands bind metal ions as schematically shown in FIG. 2, while the sulfhydryl-linked ligands bind metal ions as schematically shown in FIG. 3. The selection of a linkage site is dictated by the nature of the metal ion of interest. For those metals that favor sulfur donors over oxygen donors, a carboxylate linkage is used so as to leave a residual tridentate site consisting of the sulfhydryl group, the imine nitrogen and either an aromatic nitrogen (in the case of $L_1$ to $L_4$) or a phenolic oxygen (in the case of $L_5$ to $L_8$). For those metals that favor oxygen donors, a sulfhydryl linkage is used, leaving a residual tridentate site comprising a carboxylate oxygen, an imine nitrogen and either an aromatic nitrogen (in the case of $L_1$ to $L_4$) or a phenolic oxygen (in the case of $L_5$ to $L_8$).

TMLC's of a variety of transition and main group metal ions suitable for use as targets for MLC-specific antibody production may be constructed from both symmetrical (all ligands identical) and mixed-ligand combinations (i.e. combinations of different ligands) of the preferred ligands shown in FIG. 1. Such MLC's, when conjugated to a carrier protein are useful as immunogens for raising antibodies specific for that metal ion in complexed form. Ligands $L_1$–$L_4$ (Y=Z=Hydrogen) bear a single formal negative charge when in metal-bound form (FIG. 2), while ligands $L_5$–$L_8$ (Y=Z=Hydrogen) are doubly charged. In addition to the selection of a preferred donor atom (sulfur or oxygen), the selection of ligand electronic charge also follows from the nature of the particular metal ion of interest.

Of particular interest to the present invention are antibodies to MLC's of lead(II). Lead(II) favors sulfur donors over oxygen donors and requires only two singly charged ligands to achieve neutralization of the dipositive charge on the lead ion. Preferred antibodies that exhibit specificity for MLC's of lead(II) are raised against ternary complexes constructed from both symmetrical and mixed-ligand combinations of the ligands shown in FIG. 4.

Figure 5:
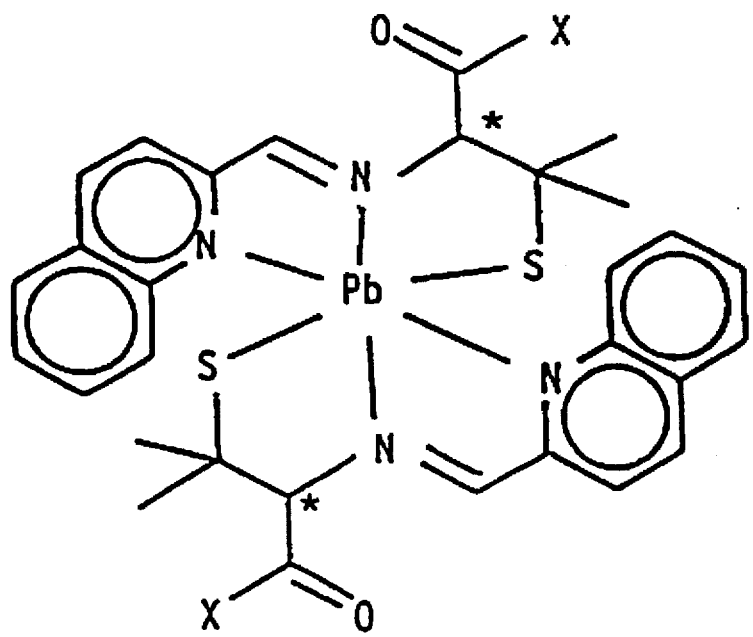
FIG. 5 shows the preferred TMLC for lead ion.

Ligands $L_9$–$L_{12}$ form electronically neutral TMLC's with lead(II) of the general formula ((Ligand)$_2$Pb). Such TMLC's can be symmetrical (($L_9$)$_2$Pb, ($L_{10}$)$_2$Pb, ($L_{11}$)$_2$Pb, ($L_{12}$)$_2$Pb) or mixed-ligand complexes ($L_9L_{10}$Pb, $L_9L_{11}$Pb, $L_9L_{12}$Pb, $L_{10}L_{11}$Pb, $L_{10}L_{12}$Pb, $L_{11}L_{12}$Pb). Particularly preferred antibodies according to the present invention recognize a symmetrical MLC based on ligand $L_9$ and having the structure shown in FIG. 5. This TMLC ($M_1$) contains two delocalized aromatic ring systems, four 5-membered chelate rings and two asymmetric carbon centers (marked with "*" on FIG. 5).

Metal Ions of Interest

Of particular interest to the present invention are antibodies recognizing those metal ions that may be found in the human bloodstream. Such metals include endogenous, essential metal ions and nonphysiologic metal ions that may be present either as a result of their use as therapeutics or because of the ingestion, absorption or inhalation of metals present in the environment. Thus, the metal ions include lead, mercury, nickel, cadmium, thallium, antimony, silver, chromium, manganese, platinum, gold, aluminum, bismuth, gallium, iron, copper, zinc, cobalt, molybdenum, selenium and vanadium ions. According to one preferred embodiment of the present invention, monoclonal antibodies specific for MLC of lead are provided.

MLC-protein conjugates

Figure 6:
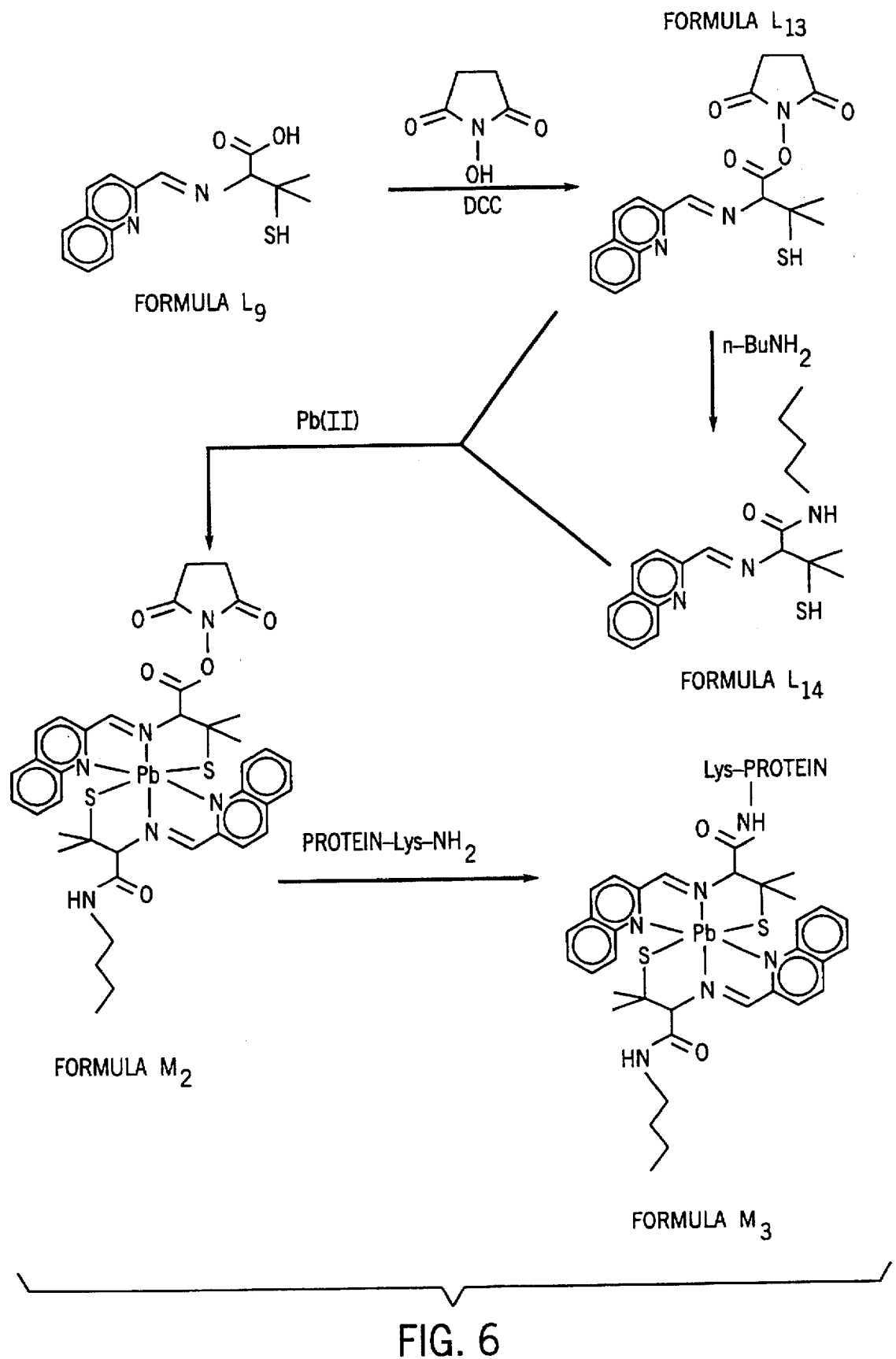
FIG. 6 presents the synthetic pathway for making a TMLC-protein conjugate, $M_3$, starting with ligands $L_9$ and $L_{13}$.

According to another aspect of the present invention, conjugates wherein a MLC is covalently linked to a protein molecule are provided. Such MLC-protein conjugates are used as immunogens and as coatings in the coated plate microtiter ELISA assays employed in screening and characterizing monoclonal antibodies of the present invention. General methods for the preparation of such MLC-protein conjugates may be illustrated using as an example the particularly preferred MLC of lead(II) shown in FIG. 5 ($M_1$). The reaction sequence used to prepare conjugates of $M_1$ with proteins is shown in FIG. 6. The protein is preferably one that can cause immunogenic response in an animal. Examples of the protein is: bovine serum albumin (BSA), keyhole limpet hemocyanin (KLH), thyroglobulin, immunoglobulin (IgG), etc. Alternatively, instead of protein, the following can be used: carbohydrates, polysaccharides, lipopolysaccharides, poly(amino) acids, nucleic acids, and the like, of sufficient size and immunogenicity. The synthetic methods for these alternatives can be arrived at by one skilled in the art based on the disclosure herein.

As shown in FIG. 6, an amide linkage is produced between one of the ligand molecules in the MLC and the protein, by conversion of the carboxylic acid group to an N-hydroxysuccinamide active ester (Formula $L_{13}$, FIG. 6). The second ligand in the MLC that is not involved in forming a covalent link to the protein is used in the form of the n-butyl amide (Formula $L_{14}$, FIG. 6). This is done to render the carboxyl group of the second ligand unavailable for metal binding and to produce a structural analog of the conjugated form of the ligand, which is bound to the protein via the 4-carbon side chain of a lysine residue (Formula $M_3$, FIG. 6). Preferred conjugation schemes involve reacting the protein with a pre-formed TMLC in which one ligand is activated (e.g. Formula $M_2$, FIG. 6). Alternatively (FIG. 7), the protein is first reacted with a free, activated ligand ($L_{13}$) and the resulting protein-ligand conjugate (Formula $L_{15}$, FIG. 7) is incubated first with the metal ion, to give the intermediate $M_4$ (FIG. 7), then with the ligand in the n-butyl amide form to give the final MLC-protein conjugate ($M_3$, FIG. 7).

Figure 7:
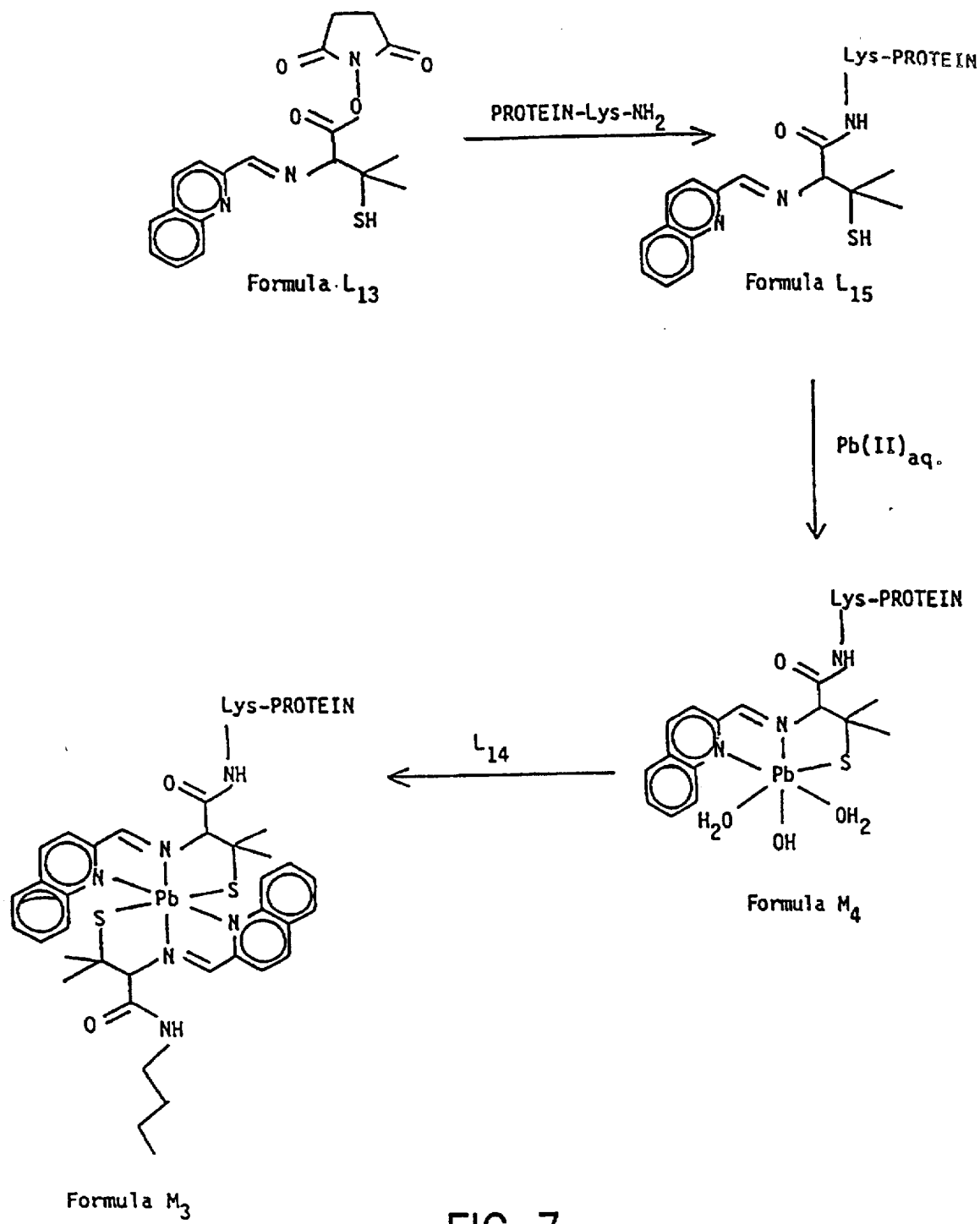
FIG. 7 presents another synthetic pathway for making the same TMLC-protein conjugate, $M_3$, starting with ligands $L_{13}$ and $L_{15}$.

When preparing MLC-protein conjugates for cross-reactivity testing purposes, a potentially cross-reactive, non-target metal ion (e.g. iron(III)) when the metal ion of interest is lead(II)) replaces the metal ion of interest in the reaction sequences shown in FIGS. 6 and 7. It is understood that in some cases, the stoichiometry of the MLC of a cross-reactive metal may not be the same as that of the corresponding MLC of the metal ion of interest.

Biological Binding Agents Such as Monoclonal Antibodies

Another aspect of the present invention relates to biological binding agents that possess specific, high affinity binding sites for MLC. Specifically, it relates to biological binding agents, such as monoclonal antibodies or recombinant polypeptides, that recognize and bind strongly to MLC comprising two or more ligands together with the metal ion of interest, i.e. TMLC and those with higher members of ligands.

These antibodies react with an epitope that combines structural features of at least two ligands in an MLC while showing minimal reactivity with either ligand individually or with the metal ion itself, i.e. these antibodies recognize an epitope that is characteristic of the fully formed MLC. In addition to interacting with the organic frameworks of at least two of the ligands in a complex, the antibody combining site may also involve the formation of one or more coordinate bonds between amino acid side chains and the metal ion, although this is not a prerequisite for obtaining antibodies that display useful metal ion specificities.

Besides whole immunoglobulins, antibodies herein include antigen binding fragments of the immunoglobulins. Examples of these fragments are Fab, F(ab')$_2$ and Fv. Such fragments can be produced by known methods.

For any given metal ion, the process of developing an antibody specific for that metal consists of: a) selecting an MLC of said metal ion that contains at least two ligands; and b) preparing an immunogen in which said target MLC is covalently linked to a carrier protein to form an MLC-protein conjugate which serves as the immunogen. Antibodies that exhibit metal ion specificity may be raised against MLC of main group metal ions, transition metal ions or metal ions of the lanthanide and actinide series of elements. The preferred immunogens are MLC-protein conjugates with more than two ligands, and more preferably the ligands are those shown in FIGS. 1 and 4, discussed above. An example of the preferred MLC-protein conjugate is described in Example 7 below.

The immunogen can be used to prepare antibodies, both polyclonal and monoclonal, according to methods known in the art for use in an immunoassay system according to the present invention. Generally, a host animal, such as a rabbit, goat, mouse, guinea pig, or horse is injected at one or more of a variety of sites with the immunogen, normally in a mixture with an adjuvant. Further injections are made at the same site or different sites at regular or irregular intervals thereafter with bleedings being taken to assess antibody titer until it is determined that optimal titer has been reached. The antibodies are obtained by either bleeding the host animal to yield a volume of antiserum, or by somatic cell hybridization techniques or other techniques known in the art to obtain monoclonal antibodies, and can be stored, for example, at −20° C.

Monoclonal antibodies can be produced by the method of Kohler and Milstein (*Nature*, 256, 495–497 (1975)) by immortalizing spleen cells from an animal inoculated with the immunogen or a fragment thereof, usually by fusion with an immortal cell line (preferably a myeloma cell line), of the same or a different species as the inoculated animal, followed by the appropriate cloning and screening steps. In the present invention, the resulting hybridomas are screened for production of monoclonal antibodies that bind to the target MLC but do not bind to the free ligands or to MLC of non-target metal ions.

Monoclonal antibodies according to the present invention offer the advantage of high specificity for the target metal ion. Specific binding to the chosen ternary (or higher molecularity) complex of the target metal ion is achievable even in the presence of a massive excess of either contaminating non-target metals or free ligands, or both. This makes it possible to configure sensitive and specific immunoassays for any metal ion of interest, by adding a combination of at least two ligands to samples thought to contain the target metal ion and using an antibody of the present invention to probe for the presence of the target MLC. The surprisingly high degree of metal ion specificity exhibited by the antibodies of the present invention is thought to arise because the greater number of degrees of freedom intrinsic in a 3-component (or higher) multimolecular complex compared to its 2-component counterpart results in a wider range of possible ligand conformations and ligand-metal stoichiometries and hence a greater likelihood that a particular shape exists that is unique to the particular metal ion of interest.

The antibodies may also be recombinant monoclonal antibodies produced according to the methods disclosed in Reading, U.S. Pat. No. 4,474,893, or Cabilly et al., U.S. Pat. No. 4,816,567. The antibodies may also be chemically constructed according to the method disclosed in Segel et al., U.S. Pat. No. 4,676,980.

More specific methods for producing polyclonal and monoclonal antibodies specific to MLC have been described in the prior art (see the discussion below, the references cited therein are hereby incorporated by reference) and can be used for the production of polyclonal and monoclonal antibodies of this invention except that the immunogens and the method for screening for the desired antibodies would be as those described in this invention. These modifications allow for the specific production and selection for antibodies which recognize an epitope which combines structural features of at least two ligands in an MLC, which are not found in the prior art. The preferred monoclonal antibodies are highly specific for a given coordination complex of a given metal ion and a given set of ligands. Preferably these antibodies recognize MLC on the basis of their shape. In addition to recognizing structural features present on at least two ligand molecules, the antibody binding site may also involve formation of one or more coordinate bonds between the metal ion and amino acid side chains of the immunoglobulin. It is not however essential that antibody side chains function as ligands in order for an antibody according to the present invention to display specificity for a given MLC.

Thus, the antibodies of the present invention overcome the problem of cross-reactivity with metal-free forms of the ligand(s) and exhibit unexpectedly high specificity for the target metal ion, which may be a main group metal, a transition metal or a member of the lanthanide or actinide series of metals. Thus, sensitive and specific immunoassays for such metals can be configured using these antibodies. These antibodies can be used, for example, to construct assays for measuring the concentration of a particular metal ion in any sample of interest. In a particularly preferred embodiment, monoclonal antibodies to MLC of lead(II) are used to construct immunoassays for levels of lead in blood, urine and other body fluids and tissues, such assays being of use in screening and monitoring concentrations of lead in the human body.

In contrast, the prior art only discloses antibodies to MLC which recognize one ligand of the MLC or the metal ion alone. The first such antibodies were described by Meares, et al, U.S. Pat. No. 4,722,892, who employed an immunogen comprising KLH conjugated to the indium(III) complex of an aminobenzyl derivative of EDTA. Antibodies were obtained that bound the In-EDTA complex with high affinity (K=4×10). Although these antibodies would also bind to EDTA complexes of metals other than indium, the affinity constant for binding to the In-EDTA complex was an order of magnitude greater than that for any other EDTA complex studied. Overall, affinity constants for binding of the antibodies to various divalent and trivalent metal ion complexes of EDTA spanned a 4 log range. Subsequent disclosures have described monoclonal antibodies raised against the cobalt(II) complex of EDTA (Goodwin, et al, *J. Nucl. Mead.*, 29, 226–34 (1988)), indium(III) complexes of DTPA (Eillette, et al, *J. Immunol. Methods*, 124, 277–82 (1989); Le Doussal, et al, *Cancer Res.*, 50, 3445–52 (1990)), iron(III) and cobalt(II) complexes of meso-tetrakis(carboxyphenyl) porphyrin (Schwabacher, et al, *J. Am. Chem. SOc.*, 111, 2344–46 1989)), N-methylmesoporphyrin IX (Cochran, et al, *Science*, 249, 781–83 (1990)), the tin(IV) complex of meso-tetrakis(4-carboxyvinylphenyl)porphyrin (Keinan, et al, *Pure Appl. Chem.*, 62, 2013–19 (1990)) and the gallium (III) complex of HBED (Zoller, et al, *J. Nucl. Med.*, 33, 1366–72 (1992)). In addition to these premeditated efforts to prepare antibodies to MLC, a polyclonal humoral anti-chelate response has been documented as an anticipated side effect in some cancer patients receiving intravenous infusions of a monoclonal antibody conjugated to the yttrium (III) complex of 1,4,7,10-tetraazacyclododecane-N,N',N"-tetraacetic acid (DOTA), a macrocyclic polyaminopolycarboxylate chelator (Kosmas, et al, *Cancer Res.*, 52, 904–11 (1992)).

The anti-porphyrin systems, all of which recognize 1:1 metal:porphyrin complexes, are of interest as potential catalytic antibodies, while the remaining anti-chelate monoclonal antibodies were developed for use in vivo, in experimental tumor therapy strategies that employ bispecific antibodies and radioisotopic metal ions, as disclosed by Meares, et al, U.S. Pat. No. 4,722,892. As such strategies require that the metal complex remain absolutely stable in vivo, chelators that form complexes of very high thermodynamic stability were selected (EDTA, DTPA, HBED). These are chelators of high denticity (6–8) and thus, in all these prior disclosures, the immunizing species were binary MLC comprising a single organic chelating ligand and a single metal ion. Potential antigenic determinants available to evoke a response to these immunogens were therefore confined to the organic framework of a single chelating ligand and, possibly, the metal ion itself.

Although it is generally expected that the organic components of an MLC will constitute the most immunogenic feature, monoclonal antibodies that recognize simple, non-chelated, "ionic" metal species have been described. Finnegan, et al, EPO0235457, disclose a monoclonal antibody to gold(I) cyanide obtained by in vitro sensitization of mouse spleen cells with the metal salt and subsequent fusion with a myeloma cell line. The resulting antibody showed 29% cross-reactivity with silver(I) cyanide. Wagner, et al, WO9010709, disclose monoclonal antibodies reactive with metal cations and in particular with Hg(II) and Pb(II). These antibodies were obtained by standard procedures from mice immunized with BSA-glutathione conjugates complexed with the metal ion of interest. In the case of mercury, it was shown that the antibody reacts with free mercuric ions, independent of coordinating agents, and thus that preformation of a mercuric ion MLC is not a requirement for monoclonal antibody recognition of mercuric ion.

The anti-chelate antibodies of the prior art exhibit properties that would severely limit their use in constructing immunoassays for metals. Foremost among these is the metal ion specificity of the immunoglobulin. A 1–2 log difference in affinity constant between the target metal and the next most reactive is likely to be inadequate for many applications, particularly those involving measurement of trace metals in biological samples where other (nontarget) metal ions may be present at levels 4 logs or more higher than the target metal. A second concern is reactivity of anti-chelate antibodies with the "empty" (i.e. non-metallated) chelating agent. In the tumor therapy applications for which most anti-chelate antibodies have been developed, such cross-reactivity presents few problems. However, in an in vitro immunoassay format, the concentration of target metal in the sample will generally be unknown and consequently a large excess of chelating agent will generally need to be added to the sample to assure complete complexation. Samples will therefore frequently contain significant concentrations of free chelator, which may in some instances exceed by several orders of magnitude the concentration of chelate in the sample. Cross-reactivity of the antibody with free chelating agent would thus give rise to artifactually high values for metal content.

Affinity Chromatography for Isolating and Purifying Antibodies Reactive with MLC Another aspect of the present invention provides affinity chromatography media composed of a TMLC covalently coupled to an appropriate solid phase. Such affinity chromatography media are used to isolate and purify monoclonal antibodies that are reactive with MLC. Using an amino-derivatized solid phase, such as aminoethyl-SEPHAROSE 4B, the same reaction sequences used to prepare MLC-protein conjugates may be used to prepare SEPHAROSE beads derivatized with MLC. As with the MLC-protein conjugates, SEPHAROSE beads may be obtained that are derivatized with either mixed or symmetrical TMLC of either the target metal ion or a cross-reactive metal ion.

Affinity chromatographic purification of monoclonal antibodies to binary EDTA-metal complexes has been reported to be difficult and Beidler, et al, U.S. 5,112,951, disclose the use of oxo acid derivatized solid supports, such as sulfopropyl resins, as an alternative means for purifying antibodies to 1:1 metal-EDTA chelates.

The affinity chromatography media of the present invention offer the advantage that the antibody may be released from the solid support under relatively mild conditions, employing any of a number of strategies. As the epitope recognized by the antibody involves the formed MLC, any process that causes dissociation of said complex can provide a basis for controlled elution of the antibody from the affinity matrix. Such processes include ligand exchange reactions in general, with those that employ small ligands with high affinity for metal ions (e.g. cyanide ion) being particularly preferred. Alternatively, a large excess of a nontarget metal ion may also be used to drive a ligand exchange reaction that disrupts the target ternary complex, causing release of the antibody from the solid phase. All such strategies result in a solid phase that, after elution of the antibody, still contains the first, covalently-coupled ligand. Regeneration of the affinity chromatography medium is therefore readily achieved by re-equilibrating the solid phase with fresh target metal ion and second (non-covalently linked) ligand.

Activity Assays

In one preferred assay configuration, MLC-protein conjugates are coated onto a solid phase and used to capture MLC-reactive antibodies. Again, using lead(II) as an example, 96-well microtiter plates are coated with a lead(II) MLC-protein conjugate (e.g. Formula $M_3$). The plate bearing the adsorbed MLC-protein conjugate is then used in an ELISA assay in which sample thought to contain murine MLC-reactive antibodies is incubated in the wells, which are then washed and exposed to an anti-mouse antibody (e.g. goat anti-mouse) that is conjugated to a signal-generating moiety (e.g. horse radish peroxidase (HRPO).

Antibodies that are reactive with the MLC of the metal ion of interest in the above assay are then further tested to establish their pattern of cross-reactivity with analogous MLC's constructed from the same ligand(s) plus a non-target metal ion. When screening, for example, tissue culture media from hybridoma supernatants for antibodies useful in the present invention, three sequential assays (either microtiter plate ELISA or FPIA) are used. The first step in the sequence employs the target MLC, either as a MLC-protein conjugate (such as MLC-BSA conjugate for ELISA) or the tracer (such as fluorescein tracer for FPIA) to identify all MLC reactive antibodies present in the tissue culture media. These MLC-reactive antibodies are then tested against the corresponding free ligand-protein conjugate (such as free ligand-BSA conjugate for ELISA) or free ligand-tracer (such as free ligand-fluorescein tracer for FPIA), and antibodies that are reactive in this assay are discarded, as they fail to meet the criterion of binding two or more ligands in an MLC. Those antibodies that are reactive with the target MLC but unreactive with the corresponding free ligand are then further screened for reactivity with analogous MLC of cross-reactive metals.

Thus, in the case of ELISA screening for a lead(II)-selective antibody, any antibody reacting with the lead(II) MLC-protein coated plate is then tested in similar assays in which microtiter plates are coated with the iron(III), copper (II) or zinc(II) analogs of $M_3$. Any antibody that reacts with the lead(II) MLC-protein coated plate is also tested for free ligand reactivity, using an analogous ELISA assay in which the ligand-protein conjugate (Formula $L_{15}$, FIG. 7) is used to coat the plate. Lead(II)-selective antibodies are identified based on their minimal reactivity with the free ligand and non-target metal plates and maximal reactivity with the lead(II) MLC plate.

Figure 8:
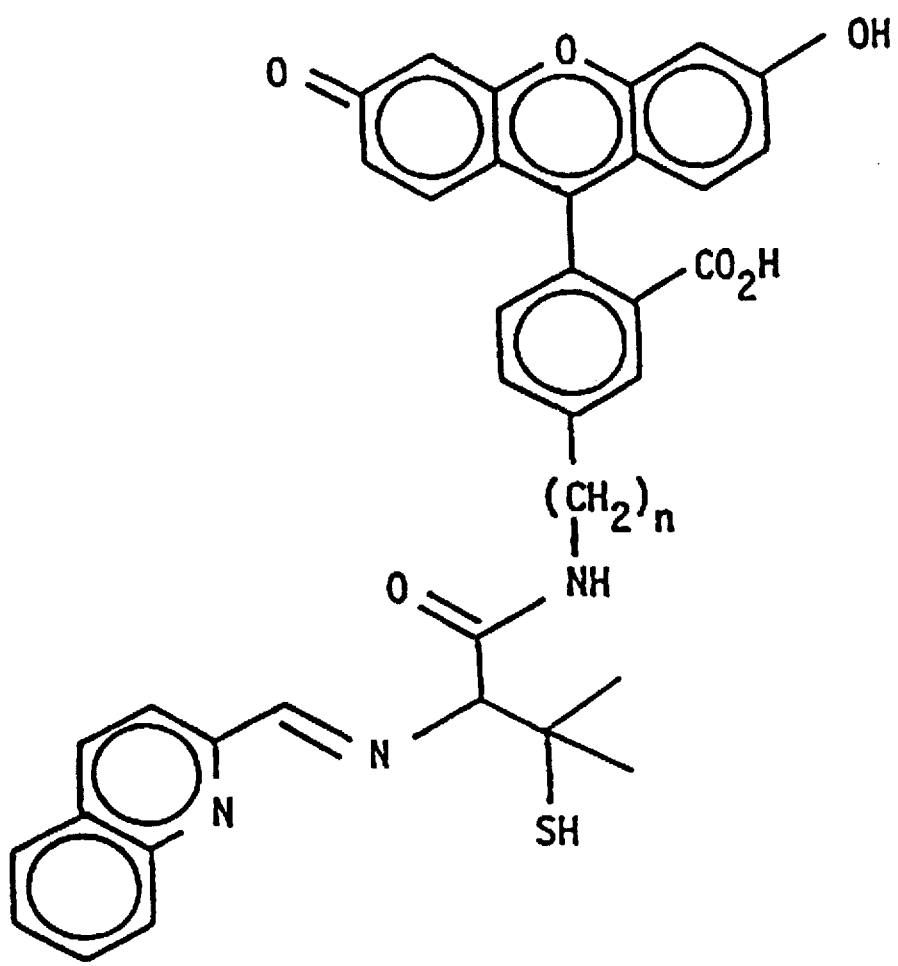
FIG. 8 presents novel fluorescein tracer $L_{16}$.

In FPIA screening, the reactivity of a sample thought to contain an $M_3$-reactive antibody would be evaluated using five fluorescent tracers: $L_{16}$ (FIG. 8), $(L_{16})_2Pb$, $(L_{16})_3Fe$, $(L_{16})_2Cu$ and $(L_{16})_2Zn$. Again, any sample causing a polarization change with $(L_{16})_2Pb$ is tested against the other tracers and antibodies are selected that produce a strong polarization change on binding $(L_{16})_2Pb$ but little or no change in the presence of $L_{16}$, $(L_{16})_2Cu$, $(L_{16})_2Zn$ or $(L_{16})_3Fe$.

Fluorescent ligand and MLC tracers

Reaction sequences analogous to those used to prepare TMLC-protein and solid phase-TMLC conjugates may also be used to obtain conjugates comprising a detectable label covalently linked to a free ligand or a TMLC. Preferred detectable labels are fluorophores, with fluorescein being particularly preferred. Examples of other detectable labels are further described below. The preparation of such fluorescein-labeled tracers may, again, be illustrated using as an example a preferred MLC of lead(II) (Formula $M_1$, FIG. 5). Thus, the activated form of the ligand (Formula $L_{13}$, FIG. 6) is reacted with either 5-aminofluorescein or 5-aminomethylfluorescein to give a ligand-fluorophore tracer (Formula $L_{16}$, FIG. 8). The corresponding MLC-fluorophore tracers can contain either one fluorescently labeled ligand (e.g. $((L_{16})(L_{14})Pb)$) or two (e.g. $((L_{16})_2Pb)$).

Figure 9:
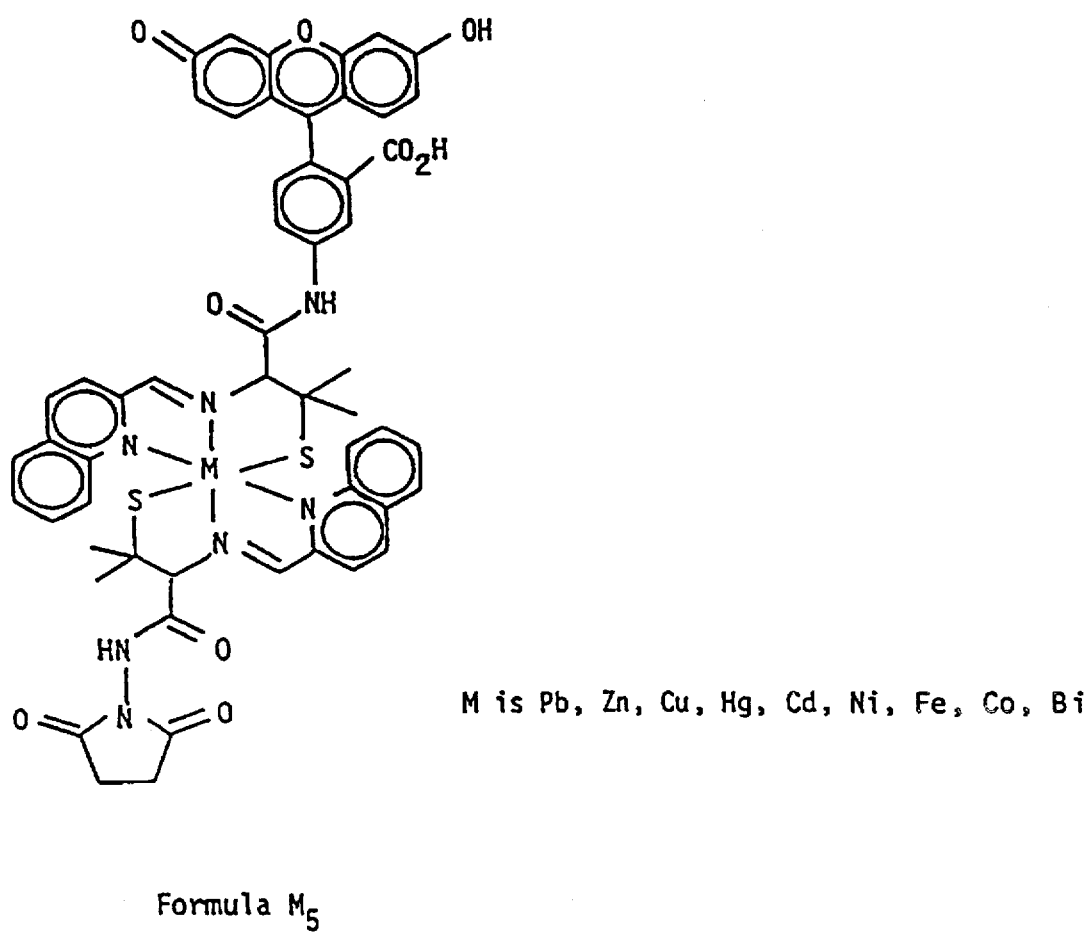
FIG. 9 presents a fluorescent labeled mixed-ligand TMLC, $M_5$.

According to one aspect of the present invention, particularly preferred fluorescently labeled mixed-ligand TMLC's have the structure shown in FIG. 9. Such TMLC's containing one fluorescent ligand and one activated, amine-reactive ligand can function in a variety of formats as selectively cleavable, metal ion dependent fluorescent labels for proteins, solid phases, polynucleotides, etc.

Figure 10:
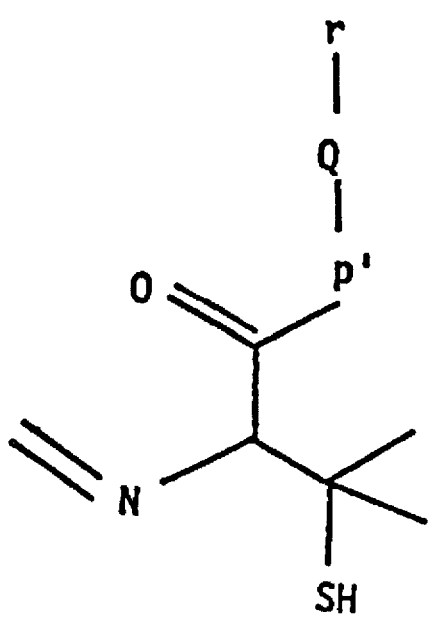
FIG. 10 schematically shows a bifunctional spacer arm attached to the carboxyl group of the ligand on the TMLC.
Figure 11:
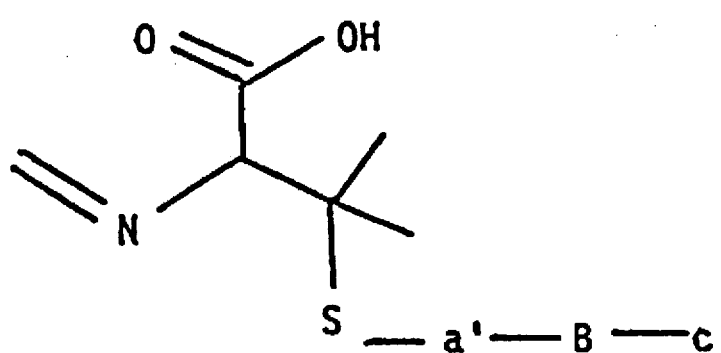
FIG. 11 schematically shows a bifunctional spacer arm attached to the sulfhydryl group of the ligand on the TMLC.

It is also understood that a spacer arm may be optionally incorporated into any MLC or ligand conjugate of the present invention, irrespective of whether that conjugate is formed with a protein, a solid phase, a fluorophore or any other such substrate. This is achieved by methods well known to the art, whereby bifunctional linkers (p-Q-r, a-B-c) are used to produce structures of the general type shown in FIGS. 10 and 11. The linkage p'-Q-r (FIG. 10) is a bifunctional spacer arm wherein p' is the residue from the reaction of one of the functional groups of the bifunctional linker (p) with the carboxylate (or activated carboxylic ester) function present in the ligand or MLC and r is a functional group that is reactive with corresponding functionalities on proteins, fluorophores, solid phases, etc. Similarly, a'-B-c (FIG. 11) is a spacer arm wherein a' is the residue functional groups of one of the functional groups of the bifunctional linker (a) with the sulfhydryl function present on the ligand or MLC. Generally, in preparing MLC or ligand conjugates of the present invention, Q and B are linking moieties consisting of from 0–50 carbon and heteroatoms, including not more than 10 heteroatoms, arranged in a straight or branched chain or cyclic moiety or any combination thereof, saturated or unsaturated, with the provisos that: (1) not more than 2 heteroatoms may be directly linked; (2) Q and B cannot contain —O—O— linkages; (3) the cyclic moieties contain 6 or fewer members, and; (4) branching may occur only at carbon atoms. Hetroatoms may include nitrogen, oxygen, sulfur and phosphorus. Examples of Q and B are alkylene, aralkylene and alkylene substituted cycloalkylene groups. c and r are chosen from the group consisting of hydroxy (—OH), carboxy (—C(=O)OH), amino (—NH$_2$), aldehyde ((—CHO) and azido (—N$_3$). a and p are selected from the group consisting of —OH, -halogen (e.g. Cl, Br, I), —SH and —NHR', where R' is selected from H, alkyl, substituted alkyl and aryl.

While fluorescent labeling is preferred, any other signal-generating moiety (chemiluminescent, radioisotopic, etc.) may be similarly conjugated to TMLC of the present invention to give tracer molecules. Said tracers are used in conjunction with antibodies according to the present invention to configure immunoassays for measuring the concentration of a particular target metal ion in any sample of interest. While any assay configuration useful in measuring low MW haptenic species can be used to measure TMLC concentrations, competition fluorescence polarization immunoassays (FPIA's) are preferred and may be used to illustrate the general procedures and principles underlying such assays:

Generally, FPIA are based on the principle that a fluorescent tracer, when excited by plane polarized light of a characteristic wavelength, will emit light at another characteristic wavelength (i.e., fluorescence) that retains a degree of the polarization relative to the incident stimulating light that is inversely related to the rate of rotation of the tracer in a given medium. As a consequence of this property, a tracer substance with constrained rotation, such as in a viscous solution phase or when bound to another solution component with a relatively lower rate of rotation, will retain a relatively greater degree of polarization of emitted light than if in free solution.

When performing a fluorescent polarization immunoassay for the specific quantification of a specific metal ion according to the present invention, a test sample suspected of containing the metal ion is contacted with the ligand(s) and antiserum or monoclonal antibodies prepared with immunogens according to the present invention, in the presence of labeled reagent of the present invention, which is capable of producing a detectable fluorescence polarization response to the presence of antiserum or monoclonal antibodies prepared with immunogens according to the present invention. Plane polarized light is then passed through the solution to obtain a fluorescent polarization response and the response is detected as a measure of amount of the metal ion present in the test sample.

Thus, the following presents an example of an FPIA for a metal:

In a sample pre-treatment procedure, the sample (which may be a biological sample and, in particular, a blood sample) is first treated to release the metal ion into an ionic, soluble form. Such treatment will generally include addition of a strong acid and/or a detergent. The resulting solution phase, containing the metal ion of interest in ionic form at low pH, is then treated with one or more ligands under conditions that favor formation of the target MLC. Such conditions will often involve neutralization of the treated sample to within the pH range of 6–9. It is often convenient to achieve this step by adding a single solution that contains the buffer salt(s) and the ligand(s), the buffer concentration (s), the concentration of each ligand and the final solution pH being selected such as to optimize formation of the target MLC. The resulting solution is then incubated together with a) a monoclonal antibody according to the present invention that is specific for the target MLC, and; b) a tracer molecule comprising the same MLC conjugated to a fluorophore. The concentration of antibody and tracer are selected such that MLC formed by the target metal present in the sample competes effectively with the tracer for a limited number of antibody binding sites, within the sample metal ion concentration range of interest. Measurement of the fluorescence polarization of the resulting solution provides a measure of the proportion of fluorophore that is bound to antibody. The concentration of target metal ion in the sample is then calculated from a standard curve that relates fluorescence polarization to metal ion concentration.

The FPIA can be conducted in commercially available automated instruments such as the IMx®, TDx®, and TDxFLx™ instruments (available from Abbott Laboratories, Abbott Park, Ill., U.S.A.).

While particularly useful in developing sensitive and specific immunoassays for metal ions, antibodies of the present invention are expected to find use in a wide variety of other applications. For example, antibodies according to the present invention are expected to be useful in separating and recovering particular metal ions from complex mixtures using immunoaffinity techniques. Thus, an antibody of the present invention could be immobilized on a solid support and the resulting affinity matrix used to recover metal ions from process streams (e.g. gold in electroplating, silver in photographic processing, etc.). Numerous such examples will be evident to those skilled in the art.

B. Other Assay Formats

In addition to FPIA, various other immunoassay formats can be followed for the quantification of a specific metal ion according to the present invention. Such immunoassay system formats include, but are not intended to be limited to, competitive, sandwich and immunometric techniques. Generally, such immunoassay systems depend upon the ability of an immunoglobulin, i.e., a whole antibody or fragment thereof, to bind to a specific analyte from a test sample with a labeled reagent comprising an antibody of the present invention, or fragment thereof, attached to a label or detectable moiety. Such detectable labels include, but are not intended to be limited to, enzymes, radiolabels, biotin, toxins, drugs, haptens, DNA, RNA, liposomes, chromophores, chemiluminescers, colored particles and colored microparticles, fluorescent compounds such as aminomethylfluorescein, 5-fluoresceinyl, 6-fluoresceinyl, 5-carboxyfluorescein, 6-carboxyfluorescein, aminofluorescein, thioureafluorescein, and methoxytriazinolyl-aminofluorescein, and the like fluorescent derivatives.

Typically, the extent of binding in such immunoassay system formats is determined by the amount of the detectable moiety present in the labeled reagent which either has or has not participated in a binding reaction with the analyte, wherein the amount of the detectable moiety detected and measured can be correlated to the amount of analyte present in the test sample. For example, in a competitive immunoassay system, a substance being measured, often referred to as an analyte, competes with a substance of close structural similarity coupled to a detectable moiety, often referred to as a tracer, for a limited number of binding sites on antibodies specific to the portion or portions of the analyte and tracer with structural similarity, shared with an immunogen employed to produce such antibodies. An example of such an assay would involve: (a) contacting a test sample (suspected of having an analyte of interest) to a labeled reagent (i.e. a tracer) and an antibody which is capable of binding the labeled reagent and the analyte, to form a reaction solution; (b) incubating the reaction solution for a sufficient amount of time to allow the antibody to bind the labeled reagent and analyte, if present; and (c) measuring the amount of the labeled reagent in the reaction solution which is bound to said antibodies as a function of the amount of the analyte in the test sample. The tracer and antibody can be added to the test sample simultaneously or sequentially, in no particular order. Preferably, the antibody is added to the test sample after the addition of the tracer. The preferred assay utilizes $M_6$ tracer with antibodies raised with $M_3$ immunogen wherein the protein is BSA. Preferred examples of the immunogens and tracers are shown in the Examples 7 and 8 respectively below.

V. Test Kits

A test kit according to the present invention comprises all of the essential reagents required to perform a desired immunoassay for the quantification of a specific metal ion in a test sample. Examples of such immunoassays include a FPIA. The test kit is preferably presented in a commercially packaged form as a combination of one or more containers holding the necessary reagents, as a composition or admixture where the compatibility of the reagents will allow.

Particularly preferred is a test kit for the FPIA quantification of a specific metal ion in a test sample, comprising any ligands, tracers, and antibodies as described in this patent application for the quantification of a specific metal ion. It is to be understood that the test kit can, of course, include other materials as are known in the art and which may be desirable from a user standpoint, such as buffers, diluents, standards, and the like.

To illustrate the invention, in the following Examples bifunctional tridentate ligands suitable for binding lead(II) are provided, together with ternary complexes of these ligands with lead(II) and monoclonal antibodies that are specific for said TMLC. A homogeneous fluorescence polarization immunoassay for measuring levels of lead in blood and other biological samples is provided, based on a monoclonal antibody that is specific for a TMLC of lead(II).

EXAMPLE 1

SYNTHESIS OF LIGAND $L_9$ (X=—OH, FIG. 6)

Quinoline-2-carboxaldehyde (15.7 g, 100 mmole) was dissolved with stirring in refluxing MeOH (140 mL). The resulting solution was stirred at reflux and a solution of D-penicillamine (14.9 g, 100 mmole) and NaOH (4.0 g, 100 mmole) in MeOH (40 mL) was added over 10 min in 1–2 mL aliquots. After stirring at reflux for a further 3 h, the solution was cooled to room temperature (herein also referred to as "RT") and concentrated to ca. 125 mL using a rotary evaporator. The resulting solution was stirred and conc. HCl (10 mL) was added in 1 mL aliquots. Addition of the final aliquot of acid produced a dense white precipitate, which was filtered off, washed with MeOH/HCl (2×30 mL) and dried under vacuum to give 20.53 g (71%) of ligand 9 (X—OH, FIG. 6). Mass. spec. (DCI) m/e 289 (M+H)$^+$, 243 (M+H —CO$_2$H)$^+$, 211 (M+H—CO$_2$H —SH)$^+$; $^1$H NMR (300 MHz, CD$_3$OD) d 8.22–8.48 (m, 1H), 8.03–8.11 (m, 1H), 7.88–7.95 (m, 1H), 7.73–7.82 (m, 1H), 7.56–7.68 (m, 1H), 7.45 (d, 1H), 5.98 (s, 1H), 4.84 (s, 1H), 4.00 (s, 1H), 1.70 (s, 3H), 1.47 (s, 3H).

Ligands $L_{10}$, $L_{11}$ and $L_{12}$ were similarly prepared using, respectively, pyridine-2-carboxaldehyde, di-2-pyridyl ketone or isoquinolyl phenyl ketone in place of the quinoline-2-carboxaldehyde in the above example.

EXAMPLE 2

FORMATION OF A SYMMETRICAL TMLC OF Pb(II) AND LIGAND $L_{10}$

A solution of ligand $L_{10}$ (X=—OH, FIG. 6, 2.38 g, 10 mmole) and NaOH (0.8 g, 20 mmole) in MeOH (40 mL) was stirred at RT and a freshly prepared solution of Pb(OAc)$_2$.3H$_2$O (1.89 g, 5.0 mmole) in MeOH (15 mL) was added drop-wise, producing a small amount of white precipitate. After stirring at RT for a further 4 h, the reaction mixture was filtered and the filtrate evaporated to dryness to give the symmetrical TMLC Pb(L$_9$)$_2^{2-}$. Yield 2.48 g (73%). Mass. spec. (FAB) m/e 727 (M+2Na)$^+$, 705 (M+H+Na)$^+$. Observed isotopic distribution patterns for both the m/e 705 and the m/e 727 parent molecular ions matched those predicted based on the 4 naturally occurring stable isotopes of lead.

EXAMPLE 3

FORMATION OF A MIXED-LIGAND TMLC: ( (L$_{10}$)(L$_{11}$)Pb)

A solution of ligand $L_{10}$ (X=—OH, FIG. 6, 1.19 g, 5.0 mmole) and NaOH (0.40 g, 10 mmole) in MeOH (20 mL) was stirred at RT and a freshly prepared solution of Pb(OAc)$_2$.3H$_2$O (1.89 g, 5.0 mmole) in MeOH (15 ML) was added as a bolus. The resulting solution was stirred overnight at RT then filtered. The filtrate was then stirred as a solution of ligand $L_{11}$ (X=—OH, FIG. 6, 1.58 g, 5.0 mmole) and NaOH (0.40 g, 10 mmole) in MeOH (30 mL) was added drop-wise. After stirring at RT for a further 2 h, the reaction mixture was filtered and the filtrate evaporated to dryness under vacuum to give the unsymmetrical TMLC ((L$_{10}$)(L$_{11}$)Pb)$^{2-}$ as a yellow solid (3.36 g, 89%). Mass spec. (FAB) m/e 804 $(M+2Na)^+$, 782 $(M+H+Na)^+$.

EXAMPLE 4

PREPARATION OF A LIGAND BEARING AN ACTIVATED GROUP FOR SUBSEQUENT CONJUGATION: SYNTHESIS OF LIGAND $L_{13}$

Ligand $L_9$ (8.64 g, 30 mmole) and N-Hydroxysuccinamide (3.45 g, 30 mmole) were suspended in THF (250 mL). The resulting mixture was stirred at RT and a solution of dicyclohexylcarbodiimide (6.18 g, 30 mmole) in THF (20 mL) was added. Stirring at RT was continued for a further 24 h, then the reaction mixture was filtered. The filtrate was concentrated under vacuum to ca. 30 mL, producing a little additional white precipitate, which was filtered off. The filtrate was then stirred and hexane (120 mL) was added drop-wise, precipitating the product as a dense white solid. This was filtered off, washed with hexane (50 mL) and dried under vacuum to give 9.54 g (83%) of ligand $L_{13}$ (FIG. 6). Mass spec. (FAB) m/e 386 $(M+H)^+$; $^1H$ NMR (300 MHz, $CDCl_3$) d 8.07–8.15 (m, 2H), 7.78–7.83 (m, 1H), 7.68–7.75 (m, 1H), 7.50–7.56 (m, 1H), 7.26–7.29 (m, 1H), 5.99 (d, 1H), 5.17 (t, 1H), 4.23 (d, 1H), 2.89 (s, 4H), 1.80 (s, 3H), 1.52 (s, 3H).

EXAMPLE 5

PREPARATION OF A BLOCKED, n-BUTYL AMIDE FORM OF A LIGAND: SYNTHESIS OF LIGAND $L_{14}$

Ligand $L_{13}$ (1.93 g, 5.0 mmole) was suspended in $Et_2O$ (60 mL) and the resulting mixture was stirred vigorously at RT for 15 min. The small amount of undissolved solid remaining at that time was removed by filtration. The filtrate was stirred and a solution of n-Butyl amine (0.37 g, 5.0 mmole) in $Et_2O$ (5 mL) was added, producing an immediate white precipitate. The reaction mixture was stirred for a further 60 sec. then was rapidly filtered. The filtrate was allowed to stand at RT undisturbed overnight, during which time the product crystallized on the walls of the flask. The mother liquor was decanted off and the crystalline product dried under vacuum to give 0.67 g (39%) of ligand $L_{14}$. Mass spec. (FAB) m/e 344 $(M+H)^+$; $^1H$ NMR (300 MHz, $CDCl_3$) d 8.07–8.15 (m, 2H), 7.78–7.82 (m, 1H), 7.68–7.75 (m, 1H), 7.50–7.55 (m, 1H), 7.35 (d, 1H), 6.72 (t, br, 1H), 5.90 (s, 1H), 3.77 (s, 1H), 3.25–3.50 (m, 2H), 1.75 (s, 3H), 1.50–1.60 (m, 2H), 1.45 (s, 3H), 1.33–1.45 (m, 2H), 0.95 (t, 3H).

EXAMPLE 6

PREPARATION OF A PROTEIN-LIGAND CONJUGATE: BSA-LIGAND $L_9$ (FORMULA $L_{15}$, FIG. 7)

BSA (50 mg, $8\times10^{-4}$ mmole) was dissolved in a buffer comprising 0.1M sodium acetate 0.1% zinc acetate (w:v), pH 5.3 (6.5 mL). Acetonitrile (2.0 mL) was added to the buffered protein solution, which did not change in either appearance or pH as a result. A solution of ligand $L_{13}$ (15.4 mg, $4\times10^{-2}$ mmole) in acetonitrile (1.5 mL) was added drop-wise to the BSA solution, and the resulting solution was incubated at RT overnight. For the first 4 h after ligand addition, the pH of the reaction solution was checked periodically and maintained in the range of 5.0–5.5. After overnight incubation, unconjugated ligand was removed by gel filtration on a 2.5×20 cm Sephadex LH-20 column equilibrated and eluted with 65%:35% (v:v) 0.1M NaOAc/ 0.1% $Zn(OAc)_2$, pH 5.3:acetonitrile. Conjugates were identified based on the characteristic ultra-violet (UV) absorbance associated with the ligand aromatic system ($\lambda_{max}$= 319,304 nm for $M_2$ in acetonitrile solution).

EXAMPLE 7

PREPARATION OF A TMLC-PROTEIN CONJUGATE: BSA-($PbL_{13}L_{14}$) ($M_3$, FIG. 6)

The following reaction is is performed under a nitrogen atmosphere up to the stage at which both ligands have been added.

Lead(II) cyclohexanebutyrate (0.56 g, 1.0 mmole) is dissolved in THF (20 mL) and the resulting solution stirred as a solution of Ligand $L_{14}$ (0.34 g, 1.0 mmole) and 1,8-bis(dimethylaminno)naphthalene (0.22 g, 1.0 mmole) in THF (26 mL) is added drop-wise. The resulting reaction mixture is refluxed for 30 min., then a solution of ligand $L_{13}$ (0.39 g, 1.0 mmole) and 1,8-bis(dimethylamino)naphthalene (0.22 g, 1.0 mmole) in THF (20 mL) is added drop-wise. After a further 30 min. reflux, the reaction mixture is cooled to RT, concentrated and filtered and the filtrate evaporated to dryness under vacuum. The residue is dissolved in acetonitrile (100 mL), to provide a stock solution of activated TMLC (Formula $M_2$, FIG. 6).

BSA (50 mg, $8\times10^{-4}$ mmole) is dissolved in 0.1M sodium acetate buffer, pH 6.0, (6.5 mL) and acetonitrile (2.0 mL) is added. An aliquot of the stock solution of $M_2$ (1.5 mL, $1.5\times10^{-2}$ mmole) is added drop-wise to the BSA solution and the resulting mixture is incubated overnight at RT. For the first 4 h after addition of the activated TMLC, the pH is monitored frequently and maintained in the range of 5.5–6.0. Unconjugated TMLC is removed after the overnight incubation by gel filtration on a 2.5×20 cm Sepharose LH-20 column, equilibrated and eluted with 65%:35% (v:v) 0.1M NaOAc, pH 6: acetonitrile. The protein-containing peak is collected and lyophilized. The lead content of the lyophilized product (Formula $M_3$, FIG. 6) is determined by atomic absorption spectroscopy.

EXAMPLE 8

Figure 12:
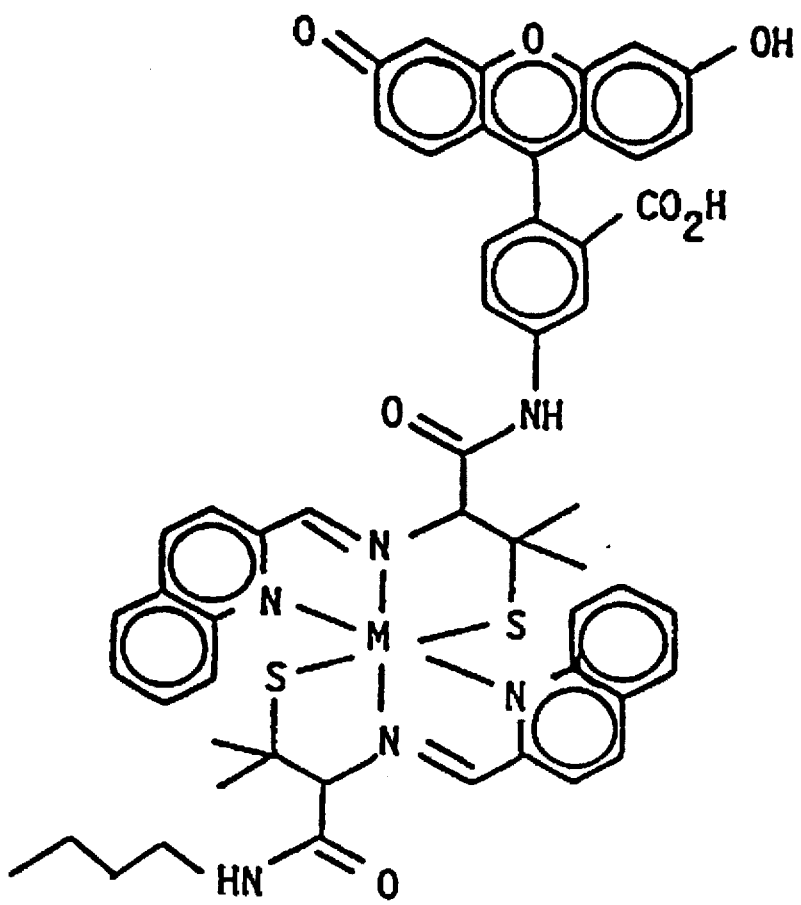
FIG. 12 presents TMLC-fluorescein conjugate $PbL_{14}L_{16}$, also denoted $M_6$.

PREPARATION OF A TMLC-FLUORESCEIN CONJUGATE: SYNTHESIS OF ($PbL_{14}L_{16}$, shown as $M_6$ in FIG. 12)

The TMLC of formula $M_2$ (1.0 mmole, FIG. 6) is prepared in THF solution as described in Example 7, The solvent is removed under vacuum and the residue redissolved in DMF (10 mL) then added to a solution of 5-aminomethylfluorescein (0.44 g, 1.0 mmole) and triethylamine (0.10 g, 5 mmole) in DMF (20 mL). The resulting reaction mixture is stirred, protected from the light, for 16 h, then evaporated to dryness under vacuum. The crude TMLC-fluorescein tracer may be purified by preparative TLC on silica plates (Baxter) eluted with $CHCl_3$:MeOH 40%:60%(v:v)

EXAMPLE 9

FLUORESCENCE POLARIZATION IMMUNOASSAY FOR BLOOD LEAD: PRETREATMENT

A blood sample to be assayed for lead content (200 uL) is treated with 3M $HNO_3$ (50 uL) and centrifuged at 2,000 g for 15 min. An aliquot of the supernatant (100 uL) is mixed with a solution of ligand $L_{14}$ (0.36 mg), prepared as described in Example 5) in borate buffer, pH 10 containing 10% (v:v) DMF (50 uL). The final pH of the resulting solution is 9.0–9.5.

EXAMPLE 10

BLOOD LEAD FLUORESCENCE POLARIZATION IMMUNOASSAYS

As described previously, the reagents for the FPIA of the present invention comprise tracers and antibodies raised against immunogens of the present invention. In addition, conventionally used assay solutions including a dilution buffer, and $M_6$ calibrators and controls are prepared.

The preferred procedure is designed to be used in conjunction with the automated TDx, ADx, or IMx systems; however, manual assays can also be performed. In both procedures, the test sample can be mixed with the supernatant after pretreatment (Example 9) and antibody in dilution buffer before a background reading is taken. The tracer is then added to the test solution. After incubation, a fluorescence polarization reading is taken.

In the automated assays, the fluorescence polarization value of each calibrator, control or test sample is determined and printed on the output tape of the TDx, ADx or IMx instrument. The instrument also generates a standard curve by plotting the polarization of each calibrator versus it's concentration, using a nonlinear regression analysis. The concentration of each control or sample is read off the stored curve and printed on the output tape.

The following reagents are used in the preferred automated blood lead assays.

1) the pretreatment solution
2) the tracer diluted in 50% methanol in potassium phosphate buffer (0.15M phosphate buffer, pH 7.5).
3) the antibody comprising rabbit antisera or mouse monoclonal antibody raised against $M_3$ (FIG. 6, wherein the protein is BSA) immunogen, diluted in TDx buffer (0.1M phosphate buffer, pH 7.5, containing 0.01% bovine gamma globulin and 0.1% sodium azide) with 30% glycerol;
4) a diluent buffer comprising TDx buffer;
5) a sets of calibrators
6) controls comprising 5 mg/mL $M_6$.

All polarized fluorescent measurements are made using the TDx instrument which performed the assay in accordance with the following protocol:

1) 22.5 mL of standard or unknown test sample and 12.5 mL of the antibody reagent delivered into the cuvette and a sufficient volume of diluent buffer is added to raise the volume to 1 mL, and a background intensity reading is taken;
2) 12.5 mL of antibody, 25 mL of the tracer, and the second 22.5 mL of sample and are added to the cuvette, and a sufficient volume of diluent buffer is added to raise the volume to 2.0 mL;
3) the reaction mixture is incubated;
4) the fluorescence polarization due to tracer binding to the antibody is obtained by subtracting the polarized fluorescence intensities of the background from the final polarized fluorescence intensities of the mixture; and
5) the polarization value for the unknown test sample is compared to a standard curve prepared using calibrators of known $M_6$ content.

The invention described herein draws on both published and unpublished work. By way of example, such work consists of scientific papers, pending patent applications, and patents. All of the works cited in this application are hereby incorporated by reference in their entirety.

The foregoing description of the presently preferred embodiments of the present invention has been offered for purposes of illustration and description. It is not intended to limit the scope of the invention, which is defined by the appended claims and their equivalents. Various modifications and variations of the preferred embodiments are possible in light of the above teachings and will be apparent to persons skilled in the art. Such modifications and variations do not depart from the spirit or scope of the invention and it is therefore intended that the scope of the invention be defined by the appended claims, including all equivalents.

We claim:

1. An affinity chromatography medium wherein a metal ion-ligand coordination complex consisting of two or more ligands, wherein said ligands are bifunctional, is covalently bonded to a solid support, said ligands being selected from the group consisting of:

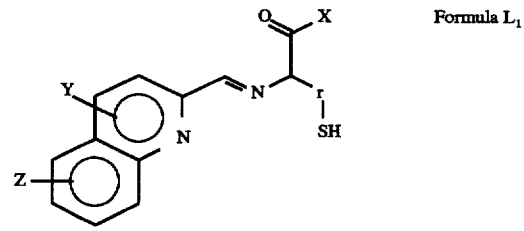

Formula $L_1$

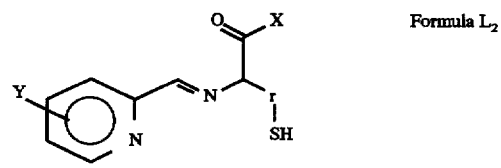

Formula $L_2$

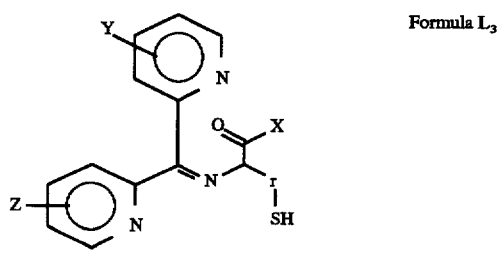

Formula $L_3$

-continued

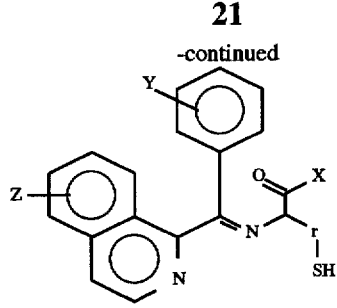
Formula L₄

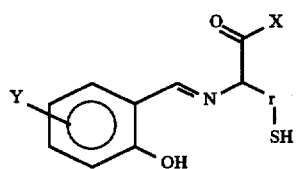
Formula L₅

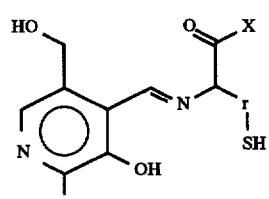
Formula L₆

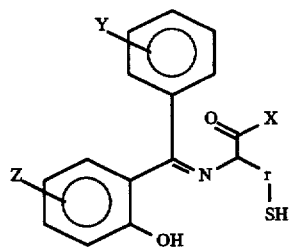
Formula L₇

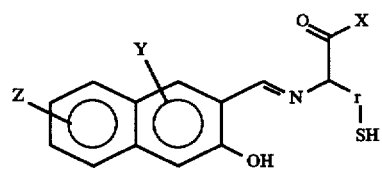
Formula L₈

Where r is selected from the group consisting of —CH₂—,
—(CH₂)₂—
—(C(CH₃)₂)—

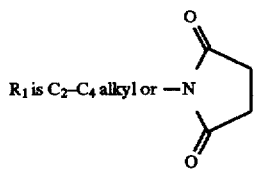

R₁ is C₂–C₄ alkyl or shown structure

R₂ is C₁–C₄ alkyl

R₃ is C₁–C₁₀ alkyl contributed by a conjugate molecule

Y and Z can be the same or different
and are selected from the group consisting of —H,
—CO₂H
—SO₃H X is selected from the group consisting of —OH,
—OR₁,
—NHR₂
—NHR₃.

2. An assay method for screening and characterizing monoclonal antibodies that are reactive with a metal ion-ligand coordination complex, comprising the steps of:

(a) covalently coupling a pre-formed metal ion-ligand coordination complex to a protein, to form a metal ion-ligand coordination complex-protein conjugate;

(b) incubating the solid phase from step (a) with a sample thought to contain monoclonal antibodies reactive with the metal ion-ligand coordination complex (c) washing the solid phase and detecting bound antibody by exposing the solid phase to anti-mouse antibody that is labeled with a signal-generating moiety; and (d) comparing the results from step (c) with those of analogous assays in which, at step (a), the metal ion of interest is replaced by a potentially crossreactive metal ion, said ligand of said metal ion-ligand coordination complex selected from the group consisting of:

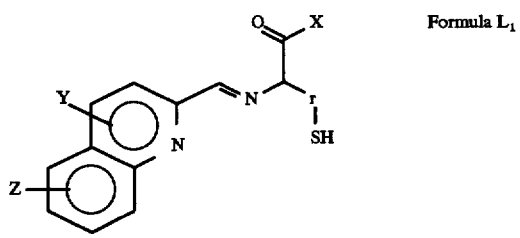
Formula L₁

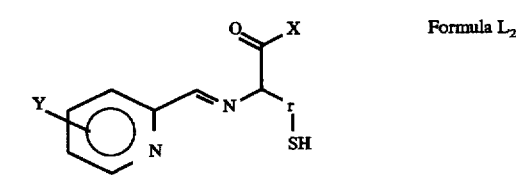
Formula L₂

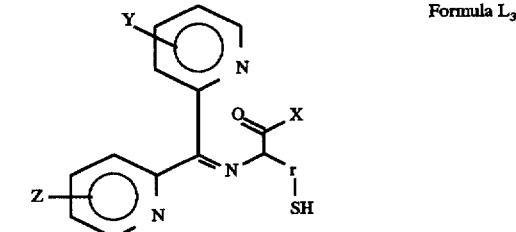
Formula L₃

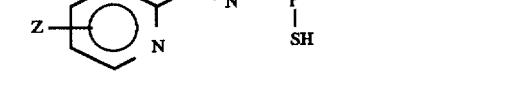

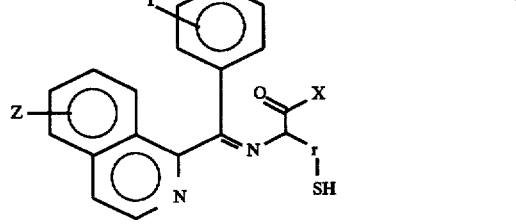
Formula L₄

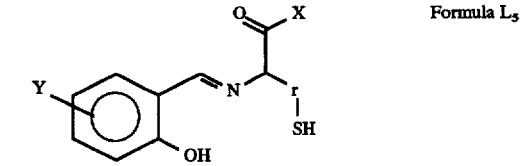
Formula L₅

-continued

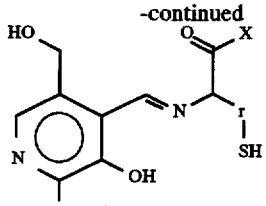

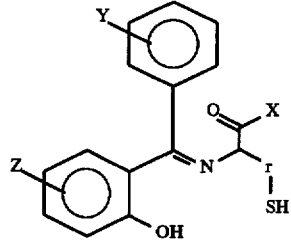

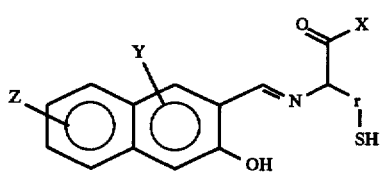

Where r is selected from the group consisting of —CH$_2$—,
—(CH$_2$)$_2$—
—(C(CH$_3$)$_2$)—

-continued

Formula L$_6$

R$_1$ is C$_2$–C$_4$ alkyl or 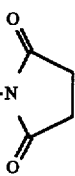

Formula L$_7$

R$_2$ is C$_1$–C$_4$ alkyl

R$_3$ is C$_1$–C$_{10}$ alkyl contributed by a conjugate molecule

Y and Z can be the same or different
and are selected from the group consisting of —H,
—CO$_2$H
—SO$_3$H Formula L$_8$ X is selected from the group consisting of —OH,
—OR$_1$,
—NHR$_2$
—NHR$_3$.

* * * * *

UNITED STATES PATENT AND TRADEMARK OFFICE
CERTIFICATE OF CORRECTION

PATENT NO. : 5,683,907
DATED : Nov. 4, 1997
INVENTOR(S) : Johnson

It is certified that error appears in the above-identified patent and that said Letters Patent is hereby corrected as shown below:

Column 21, line 50, change "$C_2$" to --$C_1$--.

Column 24, line 5, change "$C_2$" to --$C_1$--.

Signed and Sealed this

Twenty-fourth Day of March, 1998

BRUCE LEHMAN

*Attest:*

*Attesting Officer*        *Commissioner of Patents and Trademarks*